United States Patent
Linden

(10) Patent No.: US 6,234,976 B1
(45) Date of Patent: May 22, 2001

(54) DEVICE FOR EVALUATING PROTECTIVE SENSATION

(75) Inventor: Harry Linden, Santa Barbara, CA (US)

(73) Assignee: Curative Health Services, Inc., E. Setauket, NY (US)

( * ) Notice: Subject to any disclaimer, the term of this patent is extended or adjusted under 35 U.S.C. 154(b) by 0 days.

(21) Appl. No.: 08/719,167

(22) Filed: Sep. 24, 1996

(51) Int. Cl.⁷ .................................................. A61B 19/00
(52) U.S. Cl. .......................................................... 600/557
(58) Field of Search .................................. 128/740, 756; 600/553, 569

(56) References Cited

U.S. PATENT DOCUMENTS

| | | |
|---|---|---|
| D. 204,651 | 5/1966 | Laughlin . |
| D. 265,515 | 7/1982 | Levine . |
| D. 272,565 | 2/1984 | Levine . |
| D. 298,353 | 11/1988 | Manno . |
| 3,185,146 * | 5/1965 | Leopoldi ............................. 128/740 |
| 3,662,744 | 5/1972 | Low et al. . |
| 4,877,037 * | 10/1989 | Ko et al. ............................. 128/756 |
| 5,244,299 * | 9/1993 | Chu ..................................... 401/195 |
| 5,316,011 | 5/1994 | Weinstein et al. . |
| 5,381,806 | 1/1995 | Weinstein et al. . |
| 5,445,163 | 8/1995 | Machacek . |
| 5,492,132 | 2/1996 | Weinstein et al. . |
| 5,529,074 | 6/1996 | Greenfield . |
| 5,823,969 * | 10/1998 | Christy ............................... 600/557 |

OTHER PUBLICATIONS

Products for a More Productive Workplace; North Coast Industrial Health & Safety Catalog, p. 22; Summer 1994.

Sidney Weinstein, PhD; Fifty Years of Somatosensory Research: From the Semmes–Weinstein Monofilaments to the Weinstein Enhanced Sensory Test; Journal of Hand Therapy, Published by Hanley & Belfus, Inc.; Jan.–Mar. 1993.

Marsha Spivak, B.S., R.N.; Weinstein Enhanced Sensory Test & Peripheral Neuropathy; The WEST Advantage: Greater Sensitivity to Neuropathy, Copyright 1994 Connecticut Bioinstruments Inc.

*WEST Nerve Testers, Quantitative Sensory Testing Brochure*; Connecticut Bioinstruments Inc., 39–B Mill Plain Road, Danbury, Connecticut 06811.

Judith Bell–Krotoski and Elizabeth Tomancik; The repeatability of testing with Semmes–Weinstein monofilaments; The American Society of Hand Therapists; The Journal of Hand Surgery (Jan. 1987).

* cited by examiner

*Primary Examiner*—Cary O'Connor
*Assistant Examiner*—Pamela Wingood
(74) *Attorney, Agent, or Firm*—Dorsey & Whitney, LLP

(57) ABSTRACT

A device for evaluating loss of protective sensation, which comprises a probe mounted on a head that is pivotally attached to a handle member, is provided. The handle member has a protective channel. When the head is pivoted so that the device is operative, the probe extends outwardly from the handle member. When the head is pivoted into a closed position, the probe is stored within the protective channel.

1 Claim, 2 Drawing Sheets

DEVICE FOR EVALUATING PROTECTIVE SENSATION

FIELD OF THE INVENTION

The present invention relates to a device used by health care providers for detecting patients' loss of protective sensation. More particularly, it relates to an improved monofilament-type device used for this purpose.

BACKGROUND OF THE INVENTION

Protective sensation, or ability to feel pain, is a warning system that enables an individual to avoid injury and that alerts the individual when injury does occur. Certain neurological and other medical examinations require the detection of impaired or lost sensitivity. Such detection is particularly important for patients with certain diseases or disabilities. For example, nearly half of all diabetes patients in the United States develop diabetic neuropathy, a complication that suppresses a patient's ability to feel pain. Diabetic peripheral neuropathy is characterized by loss of protective sensation, which may be manifested as analgesia (absence of pain or touch sensitivity), hyposthesia (reduced sensitivity), weakness, or autonomic changes. Loss of protective sensation is that degree of sensory loss that permits cutaneous injury to occur without being perceived by the patient as painful.

When due to neuropathy, loss of protective sensation is a major permissive factor in the pathogenesis of foot injury, and often leads to ulceration, infection, and, potentially, amputation. These problems are significant: Approximately 15% of diabetes patients sustain foot or leg ulcers, and may reacquire them in the absence of preventive and protective intervention. In addition, diabetic foot ulcers account for more than 20% of total hospital days for patients with diabetes, and they are the leading cause of hospital admissions for diabetic patients. Approximately 50% of all non-traumatic amputations in the United States are caused by complications from diabetes.

Routine testing for loss of protective sensation is critical, particularly for atrisk patients, such as those with diabetes. Prior art devices, however, are cumbersome and relatively expensive, and thus hinder such routine testing. For example, the device disclosed by Low et. al, U.S. Pat. No. 3,662,744, issued May 16, 1972, telescopically extends and retracts a monofilament. This device requires the health care practitioner to turn a knob to extend the monofilament each time the device is used, to ensure the proper length of monofilament is extended from the device, and to turn the knob to retract the monofilament when done. Because the length of monofilament extended from the device is variable, the health care practitioner has difficulty knowing how much force is being exerted by the monofilament on the patient. The device also has many moving parts, and thus is relatively costly to manufacture.

The Semmes-Weinstein esthesiometer, which currently is in widespread use, also has disadvantages. The Semmes-Weinstein device consists of a monofilament that is permanently attached at a 90 degree angle to the end of a plastic rod. The monofilament is always exposed, and thus is prone to damage. To compensate, the device generally is kept in a protective case in a drawer. The result is that the device is often not conveniently accessible to the health care provider, and thus is not used on a consistent basis.

There is an unmet need for a device for evaluating protective sensation that is convenient to carry and easy to operate and clean, thereby enabling health care practitioners to evaluate routinely whether their patents have lost protective sensation. Such a device preferably also will be inexpensive, small, and lightweight.

SUMMARY OF THE INVENTION

The present invention relates to a device that tests for loss of protective sensation. The device has a probe, preferably a monofilament, with a stimulating tip at one end. The other end of the probe is attached to a pivoting head, which itself is mounted toward the end of a handle member. When the head is pivoted into its open position, the probe extends outwardly (and, preferably, generally perpendicularly) from the handle member. In this position the device is operational. When the head is rotated into the closed position, the probe is moved into a protective channel in the handle member. A pocket clip is provided to assist in making the device easy to carry.

A primary object of the present invention is to provide a device for testing for loss of protective sensation that is easily opened for operation and closed for storage. A further object of the present invention is to ensure that the probe is protected when the device is in the closed position. Another object of the present invention is to provide a testing device that is small, light, and easy to carry. Still another object of the present invention is that the device be inexpensive and simple to manufacture. It is yet another object of the present invention that the device be easy to clean, and thus reusable.

These and other objects of the present invention will become apparent with reference to the drawings, the description of the preferred embodiment, and the appended claims.

DETAILED DESCRIPTION OF THE PREFERRED EMBODIMENT

Figure 1:
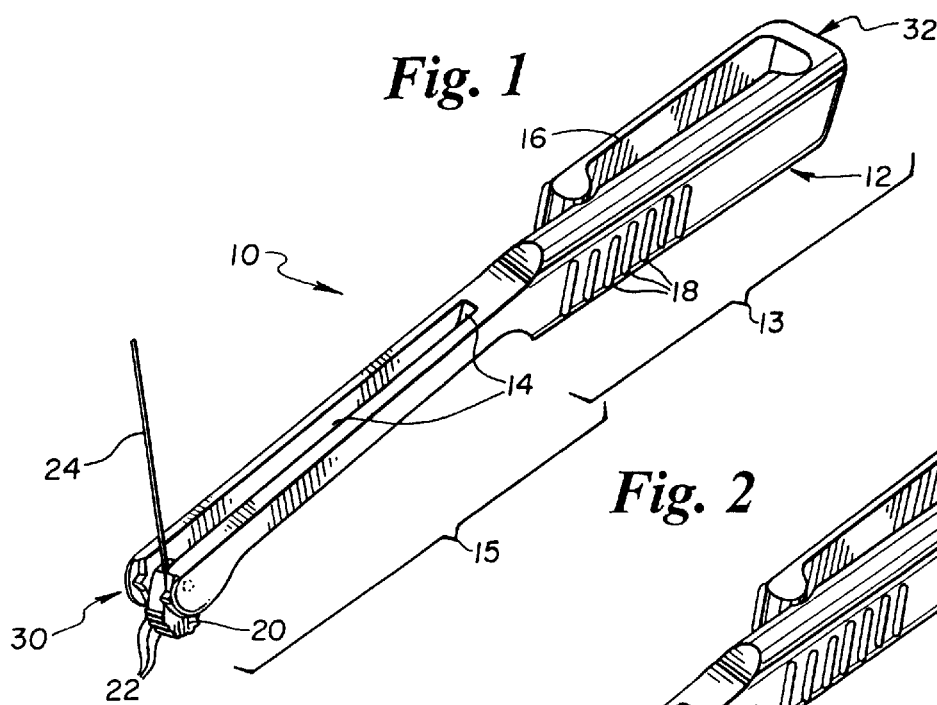
FIG. 1 is an isometric view of the present invention in its open state.

FIG. 1 depicts the sensitivity-testing device 10 of the present invention. The device 10 has a handle member 12, which is made of a generally rigid material, such as plastic. The handle member 12 has a grip portion 13 and an extension portion 15 with a channel 14 that extends from the pivot end 30 of the handle member 12 to a point located approximately midway along the handle member 12. A pocket clip 16 is located at the grip end 32 of the handle member 12. The handle member 12 and clip 16 preferably are formed into a single, continuous piece. The grip portion 13 has grip ridges 18 opposite the clip 16. In addition, the clip 16 has clip ridges (reference numeral 19 in FIG. 5) on its exterior surface. The clip ridges 19 and grip ridges 18 provide the health care practitioner a comfortable and secure grip.

A pivoting head 20 is positioned at the pivot end 30 of the handle member 12. The head 20 preferably is made of a plastic material, and it has head ridges 22 on its back. A probe 24 is permanently inserted into the front of the head 20. The probe 24 preferably is a monofilament that is relatively stiff but flexible. The preferred monofilament is generally cylindrically shaped, is approximately 38.5 millimeters in length, and is approximately 0.017 inches in diameter. The monofilament used in the present invention preferably is made of a polymeric material such as nylon. The monofilament that is preferred for the present invention has a filament index number of 5.07, and is available as Nylon 612 from DuPont. In use, a probe 24 of the preferred type applies a force to the patient's skin of 10 grams; when more than 10 grams of force is applied by the health care practitioner, the probe 24 bends, and eventually will slip off the user's skin or kink. By using a thicker or shorter probe 24, the device 10 can be made to exert greater force on the patient's skin. Conversely, when a thinner or longer probe 24 is used, the device 10 will exert less force on the patient's skin.

Figure 2:
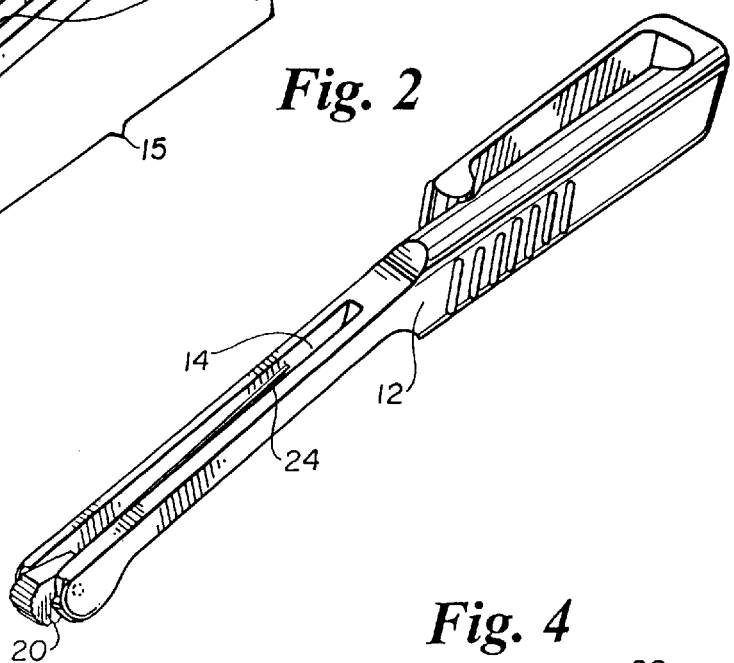
FIG. 2 is an isometric view of the present invention in its closed state.

FIG. 1 depicts the device 10 of the present invention in its open position; i.e., the probe 24 is depicted extending outwardly from the handle member 12. FIG. 2 depicts the device 10 in its closed position; i.e., the front of the head 20 has been rotated approximately 90 degrees toward the grip end 32 of the handle member 12, and the probe 24 thereby has been moved entirely into the channel 14.

Figure 3:
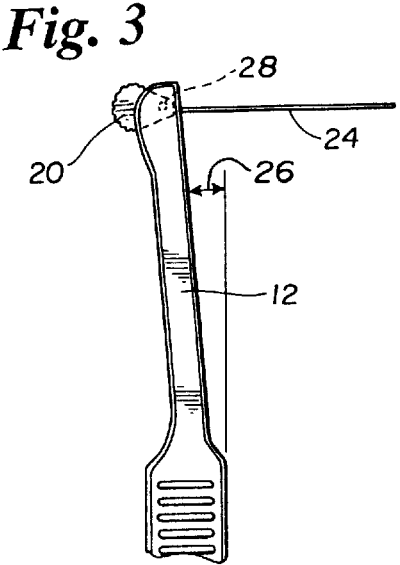
FIG. 3 is a fragmentary front elevational view of the present invention in its open state with portions shown in phantom.

As can be seen in FIG. 3, the handle member 12 is bent at a relatively small angle 26 midway along its length. When the health care practitioner holds the device 10 in a natural, comfortable manner, the angle 26 ensures that the probe 24 is in the optimal position for testing cutaneous sensitivity. The angle 26 also makes the device 10 more ergonomically comfortable for the practitioner. This angle 26 is between 0 degrees and about 30 degrees, is preferably between 0 degrees and about 15 degrees, and most preferably is about 6 degrees. The head 20 is held in place by pins 28, which may extend completely through the head 20, but preferably are only stub pins that extend from and are formed integrally with the inner surface of the channel 14. Stub pins are preferable because they permit the head 20 to be snapped into place at the pivot end 30 of the handle member 12.

Figure 4:
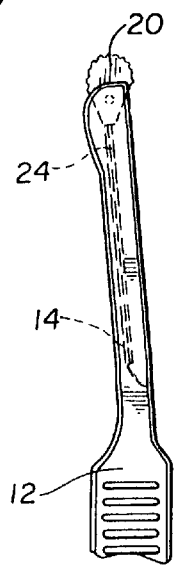
FIG. 4 is a fragmentary front elevational view of the present invention in its closed state with portions shown in phantom.

FIG. 4 depicts the device 10 in its closed position. It can be seen that, when the device 10 is closed, the probe 24 is located entirely within the protective channel 14, and thus is out of harm's way. Its nature also is concealed from the patient, who will then have no preconceived notions about the sensation he or she soon may feel. This helps ensure an unbiased response.

Figure 5:
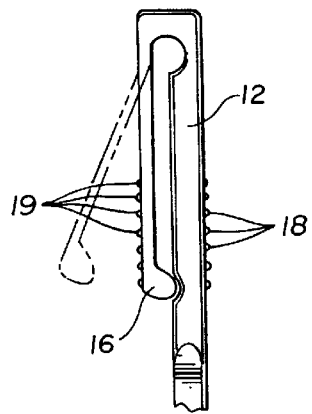
FIG. 5 is a fragmentary side elevational view.

FIG. 5 depicts the clip 16 used with the present invention. The clip 16 preferably is formed from the same material as that used for the handle member 12. FIG. 5 depicts the clip 16 in its relaxed state, as shown by the solid lines. The position the clip 16 may assume in use is shown in phantom.

Figure 6:
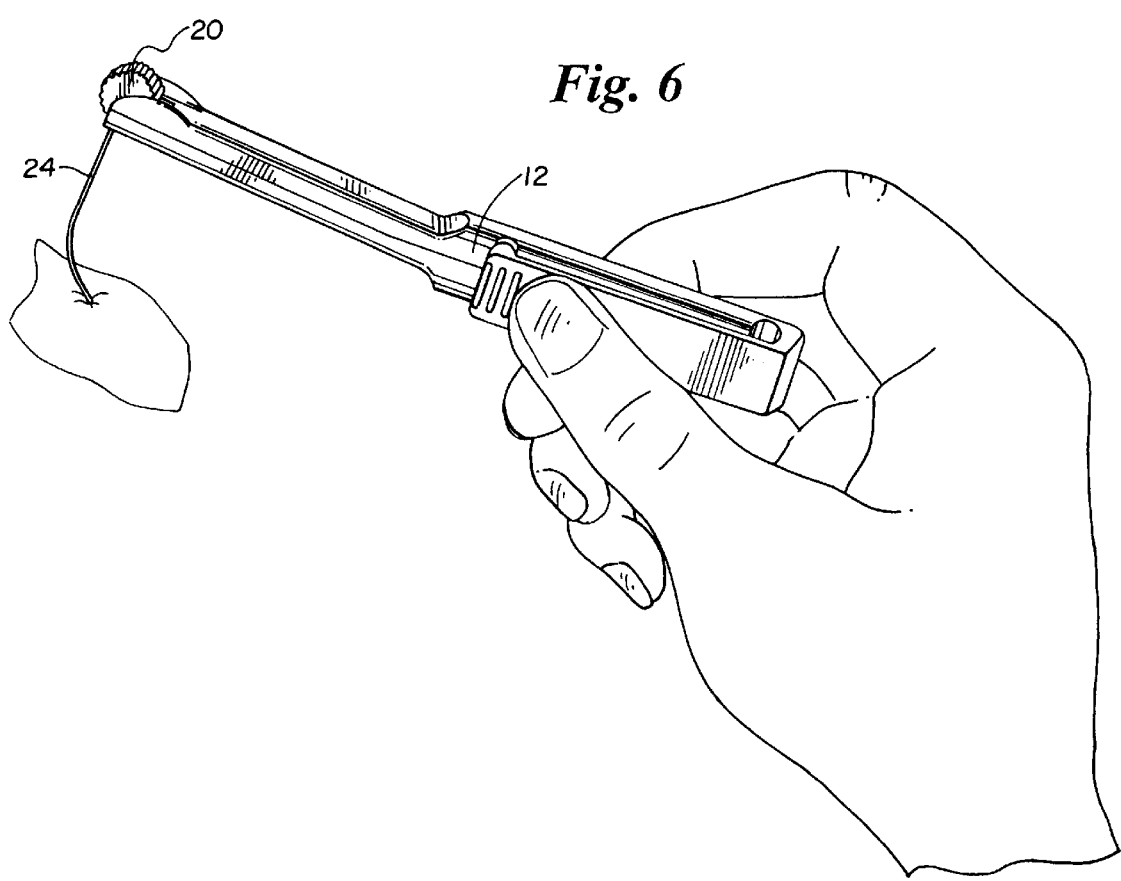
FIG. 6 is an isometric view showing the present invention in use.

The use of the present invention now will be described. To open the present invention, the health care practitioner rotates the head 20 so that the probe 24 extends outwardly from the handle member 12. This can be done with a single hand, simply by flipping the head 20 with a thumb. In use, the probe is opened and applied perpendicular to the skin, out of the patient's sight. The health care practitioner applies enough force to the handle member 12, and thereby against the patient's skin, to bend the probe 24 for approximately 1.5 seconds. As can be seen in FIG. 6, when force is applied against the patient's skin, the probe 24 will bend. Patients who cannot feel the kind of pressure applied by the device 10 have lost protective sensation, and are at increased risk for injuries that may lead to neuropathic ulcers. Upon detection of a patient's loss of protective sensation, proper medical treatment may be prescribed. After using the device 10, the health care practitioner may clean the probe 24 by wiping it with alcohol or by washing it with detergent and water. The device 10 is closed simply by rotating the head 20 with a thumb.

Although the description of the preferred embodiment has been presented, it is contemplated that various changes may be made without deviating from the spirit of the present invention. Accordingly, it is intended that the scope of the present invention not be limited strictly to that of the description of the preferred embodiment of the present invention.

I claim:

1. A hand held instrument for use by a health care examiner in test evaluation of the threshold of cutaneous sensory perception of a body surface of a human patient comprised of:

a) an instrument handle having a forward end and a rearward end, said handle provided with an elongated channel along its lower surface;

b) a pivot head member having a forward end and a rearward end, said head member being rotatably affixed proximate its rearward end to the forward end of said handle for rotational positioning of said head member alternatively between a test evaluation position and a non-test position; and c) a monofilament element of selected standard length and bending force rating affixed to and projecting from the rearward end of said pivot head member for application to a body surface area of a patient for evaluating the sensory perception thereof, said pivot head member and the forward end of said instrument handle having cooperative means for positioning said head member with its projecting monofilament in said test evaluation position whereby said monofilament element extends downwardly from said handle at an angle of about 90 degrees therefrom and for alternatively positioning said head member with its projecting monofilament in said non-test position with said monofilament element extending in a filament protected position along the length of said handle within said elongated channel.

* * * * *